US011156595B2

(12) United States Patent
Deister (10) Patent No.: US 11,156,595 B2
(45) Date of Patent: Oct. 26, 2021

(54) ORGANOTYPIC DRG-PERIPHERAL NERVE CULTURE SYSTEM

(71) Applicant: AXOGEN CORPORATION, Alachua, FL (US)

(72) Inventor: Curt Deister, Alachua, FL (US)

(73) Assignee: Axogen Corporation, Alachua, FL (US)

( * ) Notice: Subject to any disclaimer, the term of this patent is extended or adjusted under 35 U.S.C. 154(b) by 0 days.

(21) Appl. No.: 14/724,365

(22) Filed: May 28, 2015

(65) Prior Publication Data

US 2016/0349231 A1 Dec. 1, 2016

(51) Int. Cl.
| | |
|---|---|
| G01N 33/483 | (2006.01) |
| G01N 33/50 | (2006.01) |
| G01N 33/569 | (2006.01) |
| G01R 33/563 | (2006.01) |
| G01R 33/56 | (2006.01) |

(52) U.S. Cl.
CPC ..... *G01N 33/4833* (2013.01); *G01N 33/5026* (2013.01); *G01N 33/56966* (2013.01); *G01R 33/5608* (2013.01); *G01R 33/56341* (2013.01)

(58) Field of Classification Search
CPC .... G01N 33/4833; G06T 7/00; G06T 2207/00
See application file for complete search history.

(56) References Cited

U.S. PATENT DOCUMENTS

| | | | |
|---|---|---|---|
| 2001/0038835 | A1 | 11/2001 | Smith |
| 2005/0009178 | A1 | 1/2005 | Yost et al. |
| 2006/0292187 | A1 | 12/2006 | Smith |
| 2007/0155010 | A1 | 7/2007 | Farnsworth et al. |

FOREIGN PATENT DOCUMENTS

| | | |
|---|---|---|
| CA | 2422774 | 3/2003 |
| JP | 2002-087983 | 3/2002 |
| JP | 2005-500375 | 2/2005 |
| JP | 2005-508353 | 3/2005 |
| JP | 2015-509004 | 3/2015 |
| WO | WO 2003/015612 | 2/2003 |
| WO | WO 2003/031584 | 4/2003 |
| WO | WO 2013/116479 | 8/2013 |
| WO | 2014145854 A1 | 9/2014 |
| WO | WO 2015/066627 A1 | 5/2015 |

OTHER PUBLICATIONS

Hudson et al. "Optimized Acellular Nerve Graft Is Immunologically Tolerated and Supports Regeneration" Tissue Engineering, vol. 10, pp. 1641-1651.*
Deister et al. "Effects of collagen 1, fibronectin, laminin and hyaluronic acid concentration in multi-component gels on neurite extension" J. Biomater. Sci. Polymer Edn, vol. 18, No. 8, pp. 983-997 (2007).*
Schmidt et al. "Optimizing neurotrophic factor combinations for neurite outgrowth" J. Neural Eng. 3 (2006) 172-179.*
Beirowski, Bogdan et al., "Quantitative and qualitative analysis of Wallerian degeneration using restricted axonal labelling in YFP-H mice," *Journal of Neuroscience Methods*, 2004, 134:23-35.
Bozkurt, Ahmet et al., "In Vitro Assessment of Axonal Growth Using Dorsal Root Ganglia Explants in a Novel Three-Dimensional Collagen Matrix," *Tissue Engineering*, 2007, 13(12):2971-2979.
Helmchen, Fritjof et al., "Deep tissue two-photon microscopy," *Nature Methods*, Dec. 2005, 2(12):932-940.
Mukamel, Eran A. et al., "Statistical Deconvolution for Superresolution Fluorescence Microscopy," *Biophysical Journal*, May 2012, 102:2391-2400.
Simon, Neil G. et al., "Diffusion weighted MRI and tractography for evaluating peripheral nerve degeneration and regeneration," *Neural Regen Res.*, Dec. 15, 2014, 9(24):2122-2124.
Simon, Neil G. et al., "Visualizing Axon Regeneration After Peripheral Nerve Injury with Magnetic Resonance Tractography," *Neurology: Clinical/Scientific Notes*, Oct. 7, 2014, 83:1382-1384.
Torres-Espín, A. et al., "Neurite-J: An Image—J plug-in for axonal growth analysis in organotypic cultures," *Journal of Neuroscience Methods*, 2014, 236:26-39.
Alka Vyas, et al, "An in vitro model of adult mammalian nerve repair", Experimental Neurology, vol. 223, No. 1, May 21, 2009 (May 21, 2009).
Nicolas Lebonvallett, et al., "Effect of human skin explants on the neurite growth of the PC12 cell line", Experimental Dermatology, vol. 22, No. 3, Jan. 20, 2013 (Jan. 20, 2013), pp. 224-225.
Thonabulsombat, et al., "Implanted embryonic snensory neurons project axons toward adult auditory brainstem neurons in roller drum and Stoppini co-cultuers", Brain Research, Elsevier, Amsterdam, NL, vol. 1170, Sep. 11, 2007 (Sep. 11, 2007), pp. 48-58.
Richardson P M, et al., "Nerve growth activities in rat peripheral nerve" Brain Research, Elsevier, Amsterdam, NL, vol. 246, No. 1, Aug. 19, 1982 (Aug. 19, 1982, pp. 57-64, XP02425480.
European Search Report issued in European Patent Application No. 15800666.6 dated Oct. 10, 2018.

(Continued)

*Primary Examiner* — Blaine Lankford
(74) *Attorney, Agent, or Firm* — Bookoff McAndrews, PLLC (57) ABSTRACT

Techniques and systems are disclosed for a bioassay that is an in vitro mimic of peripheral nerve generation using the sensory neurons that innervate the peripheral nervous system. In some embodiments, the techniques may assist in detecting the bioactivity or potency of nerve grafts (e.g., processed, acellular human allografts) for fostering or supporting peripheral nerve regeneration. In various embodiments, techniques comprise affixing a harvested sensory neuron (e.g., a DRG) to a nerve graft segment to form a test construct; culturing the test construct in a medium; analyzing the test construct to indicate the amount of outgrowing peripheral nerve structure; and determining the potency of the nerve graft from a metric derived from the analysis. In some embodiments, techniques and materials may be used to test the effect of a varied test condition on peripheral nerve growth.

19 Claims, 4 Drawing Sheets

(56) References Cited

OTHER PUBLICATIONS

Non-Final Office Action dated Mar. 21, 2019 in counterpart U.S. Appl. No. 15/164,463.
Notice of the First Office Action dated Apr. 2, 2019 in counterpart Chinese Application Serial No. 201680034844.5.
English translation of Office Communication issued in Japanese Patent Application No. 2018-513734, dated Mar. 10, 2020.
Flint et al., "Cellular-Level Diffusion Tensor Microscopy and Fiber Tracking in Mammalian Nervous Tissue with Direct Histological Correlation," *Neuroimage*, 52(2):556-561, 2010.

* cited by examiner

ORGANOTYPIC DRG-PERIPHERAL NERVE CULTURE SYSTEM

BACKGROUND

In traumatic injuries, peripheral nerves are often damaged or severed. Techniques for the surgical repair of these nerves include direct nerve repair for small gaps, and the use of nerve grafts for larger gaps. While the axonal segment proximal to the site of the injury can regenerate new axonal sprouts, often the axonal segments distal to the injury site undergo the process of Wallerian degeneration. Wallerian degeneration involves the breakdown and clearance of nerve elements such as nonfunctional distal axons and their myelin sheaths. It is believed that axonal and myelin debris have growth-inhibitory effects that curtail nerve regeneration. Substantial evidence indicates that the clearance of nerve elements improves axonal growth in the distal nerve segment.

Nerve grafts, for example, acellular grafts, having a structure and composition similar to a nerve fascicle, can assist in axonal regeneration by providing a scaffold through which new axon segments can grow. The nerve grafts support and direct the growing axon segments, and, when acellular, provide a pathway clear of axonal and myelin debris.

Dorsal root ganglia (DRG) are the anatomical structures that contain the sensory neuron cell bodies for the sensory neurons of the peripheral nervous system.

BRIEF SUMMARY

The subject invention provides techniques and systems for a DRG-based bioassay that is an in vitro mimic of peripheral nerve generation using the sensory neurons that innervate the peripheral nervous system.

In some embodiments, the techniques assist in detecting the bioactivity or potency of nerve grafts (e.g., processed, acellular human allografts) for fostering or supporting peripheral nerve regeneration. The bioassay may be used, for instance, to establish the bioactivity of a nerve graft generally, or to validate or certify one or more aspects of the production, storage, or other processing of a nerve graft.

In certain embodiments, the methods of the subject invention comprise affixing a harvested sensory neuron (e.g., a DRG) to a nerve graft segment to form a test construct; culturing the test construct in a medium; analyzing the test construct to assess the amount of outgrowing peripheral nerve structure; and determining the potency of the nerve graft from a metric derived from the analysis.

In one embodiment, analysis can be performed by histological processing (e.g., fixing, sectioning, mounting on a slide, and staining the cultured nerve graft segment) followed by image analysis of the slide to determine the length of a farthest-outgrowing peripheral nerve structure.

In another embodiment, analysis can be performed by scanning all or part of the test construct with diffusion tensor imaging and producing tractography images identifying the outgrowing peripheral nerve structures. The amount of outgrowing peripheral nerve structure can then be quantified by, for example, measuring the length of one or more peripheral nerve structures on the image.

In another embodiment, the DRG is obtained from a fluorescent transgenic animal that expresses a fluorophore in neuronal cells. Analysis is performed by scanning all or part of the test construct with fluorescence microscopy and producing images identifying outgrowing peripheral nerve structures. The amount of outgrowing peripheral nerve structure can then be quantified by, for example, measuring the length of one or more peripheral nerve structures on the image.

In some embodiments, analysis can include a quantitative measurement of the amount of proteins or mRNA for proteins associated with an outgrowing peripheral nerve structure. For example, Schwann cells or neurites may be identified by target proteins, such as $\beta$III-Tubulin, that indicate their presence. By solubilizing the proteins (or mRNA associated with these proteins) in the test construct, an assay can determine the quantity of the protein (or associated mRNA) in the construct. This quantity is correlated to the amount of peripheral nerve structure. An ELISA or rtPCR assay, for example, can be used to determine the amount of the relevant target proteins or mRNA.

In some embodiments, techniques and materials may be used to test the effect of a varied test condition on peripheral nerve growth. Advantageously, the techniques and materials described herein can form a stable set of bioassay conditions with a baseline bioactivity. This allows the addition or variance of a condition as part of a study protocol to be tested without altering other stable bioassay conditions.

In another embodiment, a kit having certain materials for testing the effect of varied test conditions on peripheral nerve growth may be provided.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

DETAILED DESCRIPTION

Techniques and systems are disclosed for a DRG-based bioassay that is an in vitro mimic of peripheral nerve generation using the sensory neurons that innervate the peripheral nervous system.

A "bioassay" involves the use of a live animal or plant (in vivo) or a tissue or cell (in vitro) to assess the biological activity and/or ramifications of the materials and/or methods that are tested. Bioassays are typically conducted to measure the effects of a substance or methodology on a living organism.

In some embodiments of the current invention, the techniques assist in detecting the bioactivity or potency of nerve grafts for fostering or supporting peripheral nerve regeneration. The bioassay may be used, for instance, to establish the bioactivity of a nerve graft generally, or to validate or certify one or more aspects of the production, storage, or other processing of a nerve graft. For example, the bioassay may be used to recertify the bioactivity of a nerve graft after a change in production, processing, or storage parameters. The bioassay may also be used as a periodic quality control measure during the production process for a nerve graft.

In some embodiments, techniques comprise affixing a harvested sensory neuron (e.g., a DRG) to a nerve graft segment to form a test construct; culturing the test construct in a medium; analyzing the test construct to assess the amount of outgrowing peripheral nerve structure; and determining the potency of the nerve graft from a metric derived from the analysis.

Analysis of the test construct can be performed in several ways. In one embodiment, analysis can be performed by histological processing (e.g., fixing, sectioning, mounting on a slide, and staining the cultured nerve graft segment) followed by image analysis of the slide to determine the length of a farthest-outgrowing peripheral nerve structure.

In another embodiment, analysis can be performed by scanning all or part of the test construct with diffusion tensor imaging and producing tractography images identifying the outgrowing peripheral nerve structures. The amount of outgrowing peripheral nerve structure can then be quantified by, for example, measuring the lengths of one or more peripheral nerve structures on the image.

In another embodiment, the DRG is obtained from a fluorescent transgenic animal that expresses a fluorophore in neuronal cells. Analysis is performed by scanning all or part of the test construct with fluorescence microscopy and producing images identifying outgrowing peripheral nerve structures. The amount of outgrowing peripheral nerve structure can then be quantified by, for example, measuring the lengths of one or more peripheral nerve structures on the image. The length of the farthest-outgrowing peripheral nerve structures can also be quantified.

In some embodiments, analysis can include a quantitative measurement of the amount of proteins or mRNA for proteins associated with an outgrowing peripheral nerve structure. For example, Schwann cells or neurites may be identified by target proteins, such as βIII-Tubulin, that indicate their presence. By solubilizing the proteins (or mRNA associated with these proteins) in the test construct, an assay can determine the quantity of the protein (or associated mRNA) in the construct. This quantity is correlated to the amount of peripheral nerve structure. An ELISA or rtPCR assay, for example, can be used to determine the amount of the relevant target proteins or mRNA.

In some embodiments, the nerve graft is a processed nerve allograft (human) intended for the surgical repair of peripheral nerve discontinuities to support regeneration across the defect. An example of a processed nerve allograft is the Avance® Nerve Graft from AxoGen. Nerve allografts provide surgeons with a readily available nerve graft to repair peripheral nerves damaged by, for example, traumatic injury or removed during a surgical procedure.

A processed human nerve allograft is decellularized and processed, resulting in a surgical implant having the natural structural pathways to guide axon regeneration. Such nerve grafts are available in a range of lengths and diameters, and work similarly to an autograft nerve without the comorbidities associated with secondary surgical site. Processing and decellularization of the nerve allograft clears much of the axonal and myelin debris so that nerves may have an unimpeded pathway in which to regrow. Processing also removes material and molecules that may potentially elicit a deleterious immune response in the recipient.

In certain embodiments, the nerve graft may be, for example, an autograft (a nerve taken from another part of a patient's body), an isograft (a nerve taken from an identical twin), or a xenograft (a nerve taken from another species).

In some cases, positive controls can be used to demonstrate DRG viability independently of the nerve graft. Negative controls can be used to demonstrate the adequacy of analysis methods. In some cases, passivation techniques may be used to show reduced growth activity in a sample when the nerve graft is treated with inhibiting agents. The level of reduced growth activity of passivated samples can be used to assess the bioactivity of the nerve graft as a factor in nerve regeneration.

In some embodiments, techniques and materials may be used to test the effect of a varied test condition on peripheral nerve growth and regeneration. Advantageously, the techniques and materials described herein can form a stable set of bioassay conditions with a baseline bioactivity. This allows the addition or variance of a condition as part of a study protocol to be tested without altering other bioassay conditions. Analysis of the results from experiments with and without the study protocol may be conducted to assess the impact of the study protocol on peripheral nerve growth.

In some cases, a nerve graft segment may be treated in accordance with a study protocol before affixing the DRG to the end of the nerve graft segment. The study protocol may define a test condition or tested substance that is the subject of research or experimentation. The study protocol can be selected, for instance, for its potential as outgrowth inhibiting, or outgrowth promoting, or to determine the effect of the study protocol on nerve outgrowth.

For example, the study protocol may include dosing the nerve graft segment by submerging it in a solution comprising a compound (or mixture of compounds) expected to stimulate nerve growth. Examples of agents that potentially promote outgrowth, with or without a release system, include neurotrophic factors, FK506, EPO, and steroidal or non-steroidal anti-inflammatories.

The study protocol may also include dosing the nerve graft segment by submerging it in a solution comprising a compound (or mixture of compounds) expected to inhibit nerve growth. Such substances might be studied, for example, to determine the effect of environmental factors to which a patient might be exposed, or to implement control measures in a test protocol. Examples of potentially inhibitory agents include agents that degrade protein, such as a protease, materials that modify the chemical structure of the graft, such as aldehydes, or functional blocking antibodies that affect the graft or the interfacing molecules between the neuronal cells and the graft, such as integrins.

Other examples of study protocols include dosing the nerve graft segment with radiation, seeding the nerve graft segment with stem cells or Schwann cells, or exposing the regenerative construct (e.g., the nerve graft or the entire test construct) to an electrical field. By comparing the results derived under the study protocol to results not derived under the study protocol (e.g., control conditions or reference measurements), the effective bioactivity of the study protocol may be analyzed.

In another embodiment, a kit having certain materials for testing the effect of varied test conditions on peripheral nerve growth may be provided. The kit may include a nerve graft segment upon which a DRG may be placed. The user of the kit may provide the DRG, or, in some cases, the DRG may be provided as part of the kit. The kit may also include a standard medium in which to culture the nerve graft segment. The kit may also, depending on an embodiment, include one or more stains for identifying peripheral nerve structures, or protein or mRNA assay kits or components. The kit may further include detailed instructions for implementing test conditions or a study protocol within the context of the provided materials and using the described techniques.

Figure 1A:
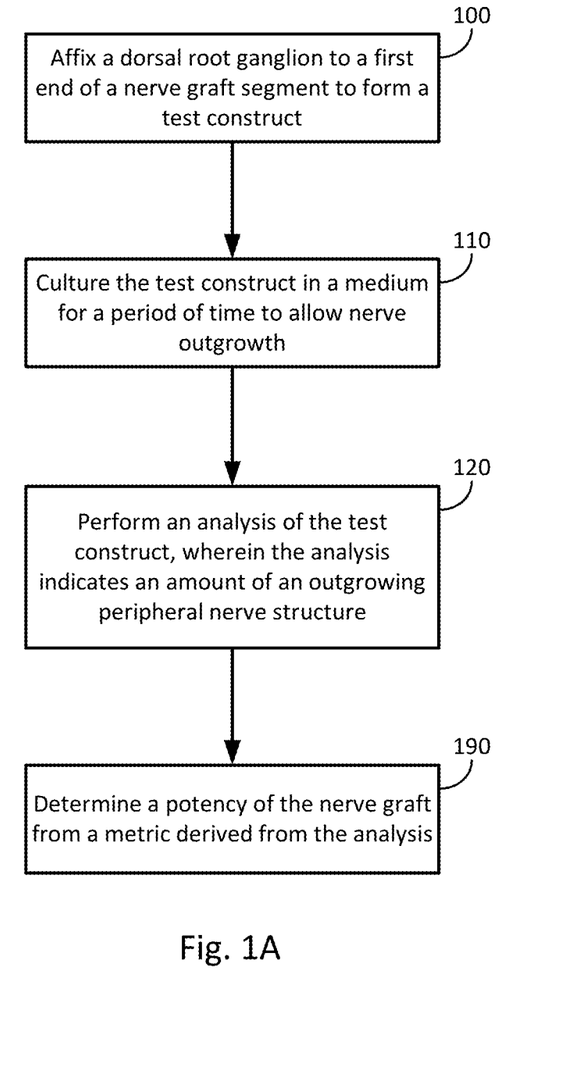
FIG. 1A shows an example process flow describing certain steps that can be performed in accordance with the bioassay of the subject invention.

FIG. 1A shows an example process flow describing certain steps that can be performed in accordance with the bioassay of the subject invention. A dorsal root ganglion (DRG) is affixed to the first end of a nerve graft segment (100). The nerve graft segment may be cut from a larger nerve graft. In some cases, for example when the nerve graft in its entirety is to be assayed, nerve graft segments may be removed sequentially and identified or tracked so that a particular segment of a particular nerve graft may be tested.

In some cases the nerve graft segment may be acellular. For example, an acellular nerve allograft may be obtained by removing nerve segments from the cadaver of an animal of the same species (here, typically human), and processing or treating them using various techniques to remove myelin and axonal debris. The processed acellular nerve allograft then contains primarily a natural endoneurial tube scaffold which supports and directs the growth of new neurites and their associated helper structures (e.g., Schwann cells).

A DRG may be obtained from a recently postnatal rat pup (see Methods and Materials). In some cases the DRG may be cleaned of nerve roots (and also the majority of the axons) and other structures, leaving primarily the cell bodies (and associated support cells such as Schwann cells) without extended neurites.

For example, in some embodiments, affixing the DRG to the end of the nerve graft segment may be performed using a drop of collagen I gel, which adheres the DRG to the end of the nerve graft so that it resists detachment while in a culture medium. Other methods of affixing the DRG to the end of the nerve graft segment may be recognized by practitioners in the art.

In some cases, the nerve graft segment may be selected to be an approximate cross-sectional diameter. A preferred size approximates twice the diameter of the rat DRG, or 1 millimeter. This preferred size allows room for the neurite to be placed and for neurite travel, while not being so large that peripheral nerve structure growth is not observed in a substantial amount of the cross section.

In some embodiments, the nerve graft segment may be treated with a passivating technique, for example, by dipping the segment in a solution containing passivating chemicals, to inhibit the bioactivity of the segment. The bioactivity of the nerve graft may be inhibited, for instance, by using a passivating agent that affects the laminin of the inner layer of the endoneurial tubes. DRG growth results from passivated vs. non-passivated samples may then be analyzed to help measure the contribution of the nerve graft segment to the nerve regeneration process.

The test construct, or sample, is formed of the nerve graft segment with the DRG attached. The test construct is cultured in a medium for a period of time (110) that is reasonable to allow neurite outgrowth from the DRG into the nerve graft segment.

In general, this type of culture is called "organotypic culture." It is a sub-type of adherent culture. There are two basic mechanisms for growing cells in vitro, adherent and suspension. In adherent cultures, cells are grown as monolayers on an artificial substrate such as tissue culture plastic or a microcarrier, which may be coated with extracellular matrix such as collagen or laminin to increase adhesion and induce growth and differentiation; in suspension cultures, the cells are free-floating in a culture medium. Most vertebrate cells are best cultured using adherent culturing. Organotypic culture allows the cells to grow three-dimensionally instead of two-dimensionally. Thus, organotypic culture may be a better mimic of true growth conditions of in vivo tissue in many instances, as the growing conditions are biochemically and physiologically more similar to in vivo conditions.

In some cases, the medium may be a "standard" medium for all samples, such as a medium containing vitamins, amino acids, nerve growth factor, and antibacterial/antimycotic agents. In other cases, the medium may include one or more neurite-growth encouraging or inhibiting substances or agents. For example, some segments of a nerve graft might be placed in a standard medium, and other segments from the same nerve graft might be placed in a standard medium containing other substances being studied to determine their inhibitory or growth-inducing effects. Results from the standard culture samples and agent under study culture samples may be compared to analyze the impact of the agent under study on nerve regeneration.

The period of time for culturing the test construct is a reasonable time to allow the neurites to measurably regenerate. This time period may range from, for example, about 3 to about 7 days. Depending on the culture conditions and other parameters, different lengths of the time period may be used, for example when a greater or lesser time period is needed to assess the impact of an "agent under study" in the medium or applied to the graft.

An analysis of the test construct is then performed to indicate the amount of outgrowing peripheral nerve structure (120). Analysis of the test construct can be performed in several ways. In some cases, for instance, the analysis can quantify the length of one or more outgrowing peripheral nerve structures into the nerve graft segment.

In some cases, the analysis can quantify the amount of peripheral nerve structure by a measurement of the amount of a relevant associated protein. Embodiments describing aspects of analyzing the test construct are described with respect to FIGS. 1B-1F, below.

The potency of the nerve graft may then be determined using a metric derived from the analysis (190). In certain cases, the metric (e.g., a distance or amount) may be compared to a baseline or to reference metric derived from a plurality of samples. In some cases, the baseline or reference metric may quantify the potency of a nerve graft under specific conditions (such as control conditions, reference conditions, passivation conditions, etc.). A comparison of the potency of the nerve graft under different conditions from the specific conditions may be performed to determine the effect or significance of the different conditions on the bioactivity of the nerve graft.

Multiple metrics from a plurality of bioassays may be analyzed statistically for experimental purposes. For example, many bioassays using numerous samples may be performed to enable a valid statistical analysis of results meeting a confidence threshold. Such experimental techniques and statistical analyses are familiar to practitioners in the art.

Figure 1B:
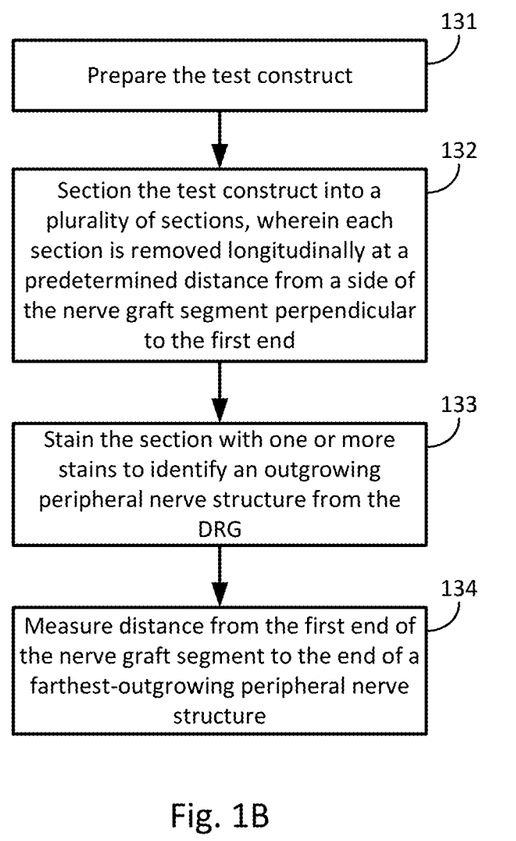
FIG. 1B shows an example method flow of an embodiment including histological processing and staining of the tissue followed by image analysis.

As noted, analysis of the test construct can be performed in several ways. In one embodiment, analysis can be performed by histological processing (e.g., fixing, sectioning, mounting on a slide, and staining the cultured nerve graft segment) followed by image analysis of the slide to determine the length of a farthest-outgrowing peripheral nerve structure. FIG. 1B shows an example method flow of an embodiment including histological processing and staining of the tissue followed by image analysis.

Following the culture period, the test construct is removed from the medium and prepared for histological processing (131). Preparing the test construct may include "fixing" the test construct. Fixing is the process of preserving tissue morphology and retaining the antigenicity of the target molecules. Fixation alters the chemical composition of tissues and often requires a compromise between preserving tissue structure and preserving the epitope. Underfixation can allow degradation of target proteins in the tissue, but overfixation can result in masking the epitope or can cause non-specific background staining when stains are applied to the sample. The method and timing of fixation are factors in sample preparation.

In some embodiments, the test constructs are formalin fixed and paraffin-embedded to allow sectioning. One fixative for paraffin-embedded tissues is neutral buffered formalin (NBF). This is equivalent to 4% paraformaldehyde in a buffered solution plus a preservative (methanol) which prevents the conversion of formaldehyde to formic acid. Paraffin embedding includes placing the tissue sample or test construct on a paraffin block that has been softened with heat, covering the test construct with molten paraffin, and allowing the paraffin to harden. Once embedded, the sample may be sectioned into thin slices for microscopy.

An alternative method of preparing the sample for sectioning and histology is cryosectioning. A sample prepared for cryosectioning is flash-frozen in a mold and may be fixed using various substances, including precipitation fixatives such as acetone as an alternative to aldehydes such as NBF. Fixation using NBF, paraffin embedding, and cryosectioning are techniques that are familiar to practitioners in the art.

Figure 2:
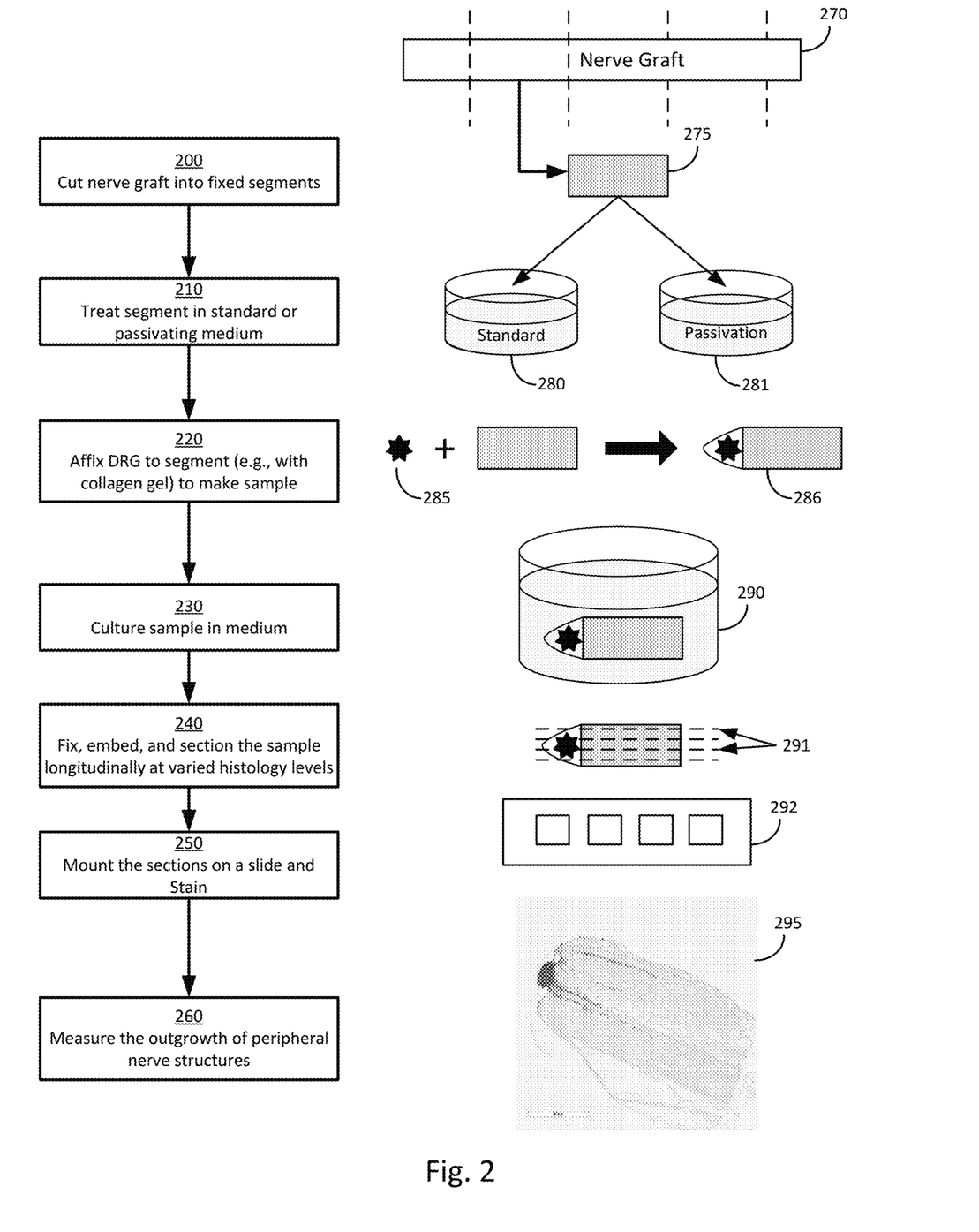
FIG. 2 shows a diagram of certain materials and the associated methods that may be used in an experiment including an immunohistochemical analysis of the test construct.

The prepared test construct is sectioned into several sections longitudinally (132) for staining. Each section has a given thickness and is taken at a given level, or depth into the sample. The longitudinal sectioning is performed down the DRG-nerve graft test construct, i.e., sections are removed at given distances along a near parallel line from a side perpendicular to the end on which the DRG was placed. FIG. 2, element 291 shows dotted lines indicating the orientation of the longitudinal segments. This sectioning technique produces slices through the test construct that can contain the length of one or more neurites growing from the DRG.

Sections are taken at several levels, i.e., distances from a perpendicular side to the first end where the DRG was placed. The various levels are selected so that a representative sample of the neurite growth down the whole of the cross-section of the nerve graft section is obtained. For example, in some cases the sections may be removed at 200 (Level 1), 400 (Level 2), 600 (Level 3), and 800 (Level 4) microns depth into the sample.

Sections are of a thickness appropriate for light microscopy. In some embodiments, the sections are from about 4 um to about 8 um thick. Sectioning of the test construct may be performed for paraffin-embedded samples using a microtome.

The removed sections can be placed on a slide and stained with one or more stains to identify outgrowing or re-growing peripheral nerve structures from the DRG into the nerve graft segment (133). Peripheral nerve structures can include, for example, neurites and the Schwann cells that produce myelin. Several methods of staining may be used to identify peripheral nerve structures, for example βIII-Tubulin antibody staining, PGP9.5 antibody staining, and S100 antibody staining.

βIII-Tubulin Antibody Staining. One type of βIII-Tubulin stain is TU-20. TU-20 is a mouse monoclonal $IgG_1$ which is raised against amino acids 441-448 of βIII-Tubulin of human origin.

PGP9.5 Antibody Staining. Protein gene product (PGP9.5) is a neuron specific protein, structurally and immunologically distinct from neuron specific enolase. Standard immunohistochemical techniques have demonstrated the presence of PGP9.5 in neurons and nerve fibers at all levels of the central and peripheral nervous system, in many neuroendocrine cells, as well as in other body cells. This antibody is of value as a marker for neurons.

S100 Antibody Staining. The S100 proteins are a family of low-molecular-weight proteins found in vertebrates and characterized by two calcium-binding sites that have helix-loop-helix conformation. S100 proteins are normally present in cells derived from the neural crest, such as Schwann cells and melanocytes. An S100 antibody stain shows the presence of normal human Schwann cells.

It should be noted that experimental factors may affect the choice of stain(s). For instance, paraffin embedding, while having certain technical advantages over cryosectioning, may affect stain response. Substances used in paraffin embedding (e.g., alcohols, aldehydes) may denature or impact the structure of certain proteins that cause the reaction response in some types of antibody staining. Cryosectioning may affect staining differently, resulting in a different choice of stains.

A distance from the first end of the nerve graft segment (i.e., the end on which the DRG was placed) to the end of a farthest-outgrowing peripheral nerve structure may then be measured (134). In some cases, a single slide may contain all the longitudinal sections taken from a particular test construct to assist in identifying the farthest-outgrowing peripheral nerve structure. Additional standard techniques may also be used, such as imaging the slide so that standard image processing software can assist in determining the distances. A human assessor may examine the image carefully in order to determine the location of the farthest growth of an outgrowing peripheral nerve structure.

In some cases, more than one farthest-outgrowing peripheral nerve structure may be measured for a given test construct. For example, the three longest structures present across all of the longitudinal sections for a particular test construct may be identified and averaged, and the average may be recorded as the measured distance for that sample.

Distance measurements of more than one type of peripheral nerve structure may be recorded. For example, in cases where staining for both neurites and Schwann cells is used, the farthest outgrowth of either neurites, Schwann cells, or both may be measured and recorded.

Figure 1C:
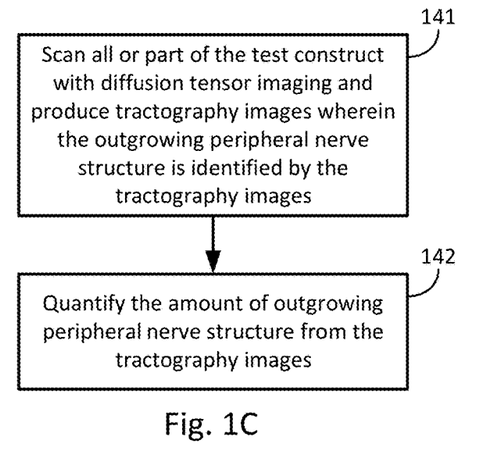
FIG. 1C shows an example process flow for an alternative embodiment using diffusion tensor imaging.

FIG. 1C shows an example process flow for an alternative embodiment using diffusion tensor imaging. In an embodiment as shown in FIG. 1C, the analysis can be performed by scanning all or part of the test construct with diffusion tensor imaging and producing tractography images identifying the outgrowing peripheral nerve structures (141).

Diffusion tensor imaging (DTI) with tractography is a type of MRI that can help to visualize nerve pathways by measuring the anisotropy of water diffusion in nerve tracts with longitudinally oriented fibers. Water diffuses freely along the longitudinal axis of a nerve tract, but is restricted by the myelin sheath in the perpendicular plane. The directionality of diffusion can be determined by applying diffusion-sensitizing gradients from multiple directions, allowing modeling of the diffusion tensor. Fractional anisotropy maps can then be calculated from the tensor, and tractography images can be produced by modeling the direction of maximum diffusivity across voxels. These tractography images can be used to visually depict neurite growth.

Once a visual depiction of outgrowing neurites has been obtained, the amount of outgrowing peripheral nerve structure can then be quantified (142), for example, by measuring the lengths of one or more peripheral nerve structures on the image. In some cases, the farthest-outgrowing peripheral nerve structure can be measured. In some cases, more than one farthest-outgrowing peripheral nerve structure may be measured for a given test construct. For example, the three longest structures present across all of the longitudinal sections for a particular test construct may be identified and averaged, and the average may be recorded as the measured distance for that sample. Additional metrics can also be computed, such as the aggregate length of neurite growth and the average length per neurite.

Figure 1D:
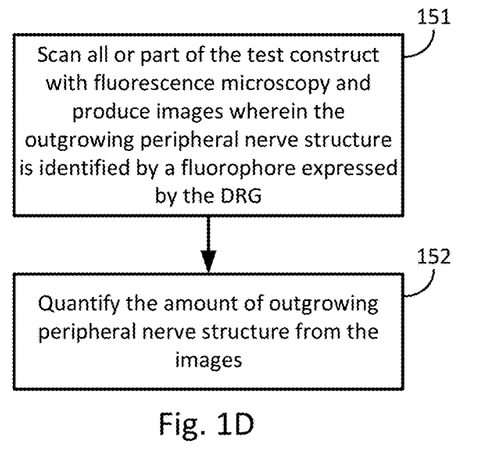
FIG. 1D shows an example process flow for an alternative embodiment using fluorescence microscopy.

FIG. 1D shows an example process flow for an alternative embodiment using fluorescence microscopy. In an embodiment as shown in FIG. 1D, the DRG is obtained from a fluorescent transgenic animal that expresses a fluorophore in neuronal cells.

A fluorophore is a fluorescent chemical compound that can re-emit light upon light excitation. Transgenic animals can be obtained for laboratory study that express fluorophores in various neuronal subsets. As peripheral nerve structures outgrow from the DRG into the nerve graft, the fluorophores are present in growing cellular structures such as axons. When viewed under fluorescence microscopy, these cellular structures are brightly and homogenously fluorescent along their full length. Examples of fluorophores that are used to show neuronal structures are yellow fluorescent protein (YFP), green fluorescent protein (GFP), and cyan fluorescent protein (CFP).

Analysis is performed by scanning all or part of the test construct with fluorescence microscopy and producing images identifying outgrowing peripheral nerve structures as indicated by the brightly-lit fluorophores. Types of fluorescence microscopy can include, for example, confocal fluorescence microscopy, two-photon fluorescence microscopy, and super-resolution fluorescence microscopy with statistical deconvolution.

The amount of outgrowing peripheral nerve structure can then be quantified (152), for example, by measuring the lengths of one or more peripheral nerve structures on the image. In some cases, the farthest-outgrowing peripheral nerve structure can be measured. In some cases, more than one farthest-outgrowing peripheral nerve structure may be measured for a given test construct. For example, the three longest structures present across all of the longitudinal sections for a particular test construct may be identified and averaged, and the average may be recorded as the measured distance for that sample. Additional metrics can also be computed, such as the aggregate length of neurite growth, the average length per neurite, and/or the quantity of fluorescent pixels in the image.

Figure 1E:
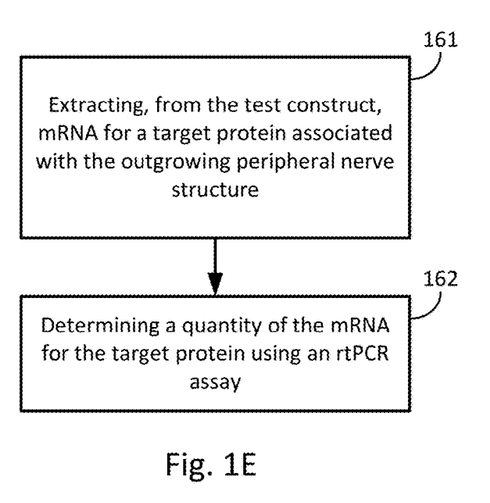
FIG. 1E shows an example process flow for an alternative embodiment using detection of mRNA for a target protein associated with outgrowing peripheral nerve structure.

FIG. 1E shows an example process flow for an alternative embodiment using detection of mRNA for a target protein associated with outgrowing peripheral nerve structure. The mRNA being measured is chosen such that its measurement is correlated with outgrowth of peripheral nerve structures. A target protein associated with outgrowing peripheral nerve structure, such as a Schwann cell or neurite, can include, for example, βIII-Tubulin, S100, and GAP-43.

In FIG. 1E, mRNA related to the target protein is extracted from the test construct (161). Extraction includes solubilizing the analyte molecule(s) present in the test construct (here, the mRNA for the target protein) for subsequent detection by an assay. Depending on the type of assay, various kinds of solvent may be used. If using an rtPCR assay, for example, a protease-based or phenol-based solvent can be used to solubilize the mRNA.

The supernatant from the extraction process is then used in an mRNA assay, such as a standard rtPCR assay. In an rtPCR assay, the mRNA is amplified, detected, and quantified (162). The quantity of mRNA from the rtPCR assay, as it is proportional to the amount of outgrowing peripheral nerve structure, can be used to determine the potency of the nerve graft.

Figure 1F:
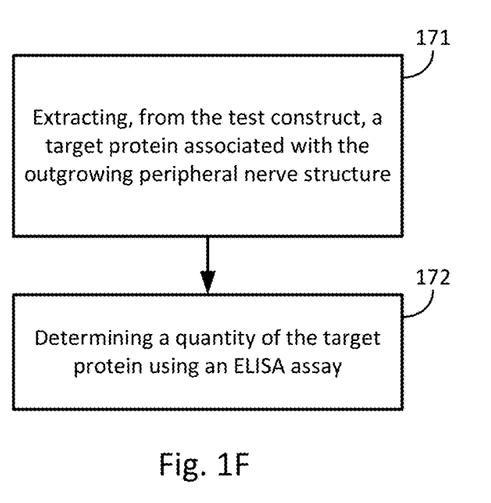
FIG. 1F shows an example process flow for an alternative embodiment using detection of a target protein associated with outgrowing peripheral nerve structure.

FIG. 1F shows an example process flow for an alternative embodiment using detection of a target protein associated with outgrowing peripheral nerve structure. The protein being measured is chosen such that its measurement is correlated with outgrowth of peripheral nerve structures. A target protein associated with outgrowing peripheral nerve structure, such as a Schwann cell or neurite, can include, for example, βIII-Tubulin, S100, and GAP-43.

In FIG. 1F, a target protein is extracted from the test construct (171). Extraction includes solubilizing the analyte molecule(s) present in the test construct (here, the target protein) for subsequent detection by an assay. Depending on the type of assay, various kinds of solvent may be used. If using an ELISA assay, for example, a urea-based or guanidine-based solvent can be used to solubilize the protein.

The supernatant from the extraction process is then used in a quantitative protein assay, such as a standard ELISA assay (172). The quantity of protein from the ELISA assay, as it is proportional to the amount of outgrowing peripheral nerve structure, can be used to determine the potency of the nerve graft.

Techniques of measuring a target protein or mRNA relating to a target protein using an rtPCR assay and an ELISA assay are understood by practitioners in the art.

Experiments:

Experiments were conducted to determine the ability of the bioassay methods to assess the quality of a nerve graft and/or the effect of a test condition in an embodiment comprising histological preparation, staining, and sectioning. In some cases, preliminary experiments also were conducted to refine the characteristics of certain bioassay parameters. For example, positive and negative controls, passivation techniques, culture conditions, and histology preparation and staining techniques were assessed and tested. Advantages of the techniques may be illustrated from results obtained from the experiment. Details of those experiments are described below. Examples and experiments should not be construed as limiting.

Materials and Methods

FIG. 2 shows a diagram of certain materials and the associated methods that may be used in an experiment including an immunohistochemical analysis of the test construct. As shown in FIG. 2, the method flow of the experiment generally includes, except in positive or negative controls: cutting a nerve graft into fixed segments (200); treating each segment in standard or passivating media (210); affixing a DRG to a segment to make a test sample (220); culturing the sample in media (230); fixing, embedding, and sectioning the sample longitudinally at various histology levels (240); mounting the sections on a slide and applying one or more stains (250); and measuring the outgrowth of peripheral nerve structures (260).

The nerve grafts 270 used in each experiment were Avance® Nerve Grafts from AxoGen®. The nerve grafts 270 were cut into approximately 3 mm segments (e.g., element 275) from one larger nerve graft 270 ranging from 30-70 mm in length. The first segment 275 was taken closest to the graft edge but did not include the end of the original graft; the next segment was taken adjacent to the first segment, and each subsequent segment was taken adjacent to the previous segment. After all of the segments were collected, they were stabilized for DRG 285 placement on the end of the segment, forming the sample/test construct 286.

Postnatal day 3 to 7 rat pups were used as the source of the DRGs (e.g., 285), as these DRGs are of sufficient size for handling with a dissecting microscope. The source rat pups are also of a sufficiently young age that the explants are capable of the high migration rate of neurites from the DRG 285 body that is conducive to the assay. DRGs may be collected from multiple pups but DRGs from each pup are pooled separately. DRGs from a single pool are consumed before using the next pool. Charles River CD rat pups were used in experimentation. The "Charles River CD Rat" is the trade name of Charles River Laboratories International's closed Sprague-Dawley colony.

Culturing

Varying the time in culture and the neurotrophic factor content of the media 290 was attempted as a means of increasing the bioassay signal (i.e. distance or amount of migration/outgrowth). Culture was conducted in a chemically defined medium 290 derived from Neurobasal media supplemented with B27, glutamine, antibiotics/antimycotics. "Standard" culture used 25 ng/mL Nerve Growth Factor (NGF) in the media 290.

Initially, a 3-day culture incubation period and a 7-day culture incubation period (with the medium changed on the 3rd day) in standard medium 290 were tested. The samples cultured in Standard media showed neurite/Schwann cell outgrowth well into the nerve graft segment at 7 days. The 3-day Standard culture samples showed less neurite/Schwann cell density than the samples cultured at 7 days.

Histology and Staining

After culturing, all the samples were prepared for histological sectioning and staining. All of the samples were embedded in paraffin and sectioned longitudinally (e.g., 291). In preliminary experimentation, paraffin-based histology was performed utilizing 4 µm or 8 µm thick sections. The sections were removed at levels 200 (Level 1), 400 (Level 2), 600 (Level 3), and 800 (Level 4) microns into the sample.

The sections 291 were affixed to a slide 292. All four levels were placed on the same slide, and each sample was placed on a different slide. The samples were embedded with the endoneurial tubes parallel with the intended cutting plane, resulting in longitudinal sections through the samples.

The sections were stained using one or more stain to identify neurite outgrowth and supporting Schwann cells. In preliminary experiments, PGP9.5 or βIII Tubulin was used to identify neurites and S100 was used to identify Schwann cells.

The slides 292 were then scanned to capture an image of the entire slide. The images 295 were used to measure the length of neurite and Schwann cell outgrowth from the edge of the segment closest to the DRG to the farthest tip of a single neurite track or the location of a Schwann cell. A qualitative score was also assigned to describe neurite and Schwann cell outgrowth.

Controls

Positive controls were used to demonstrate the viability of the DRGs used in the assay under the same culture conditions used on the nerve graft segments, but without the use of a nerve graft.

A commercial preparation of Engelbreth-Holm-Swarm (EHS) mouse sarcoma cell extracellular matrix (ECM), which is available from several suppliers (e.g., Matrigel from Corning Life Sciences, Cultrex BME from Trevigen, or ECM gel from Sigma), was used in the positive controls. These preparations are liquid when refrigerated, but gel at ambient conditions (or 37° C.). The EHS extracellular matrix is essentially a solubilized basement membrane that is high in laminin-111 and collagen IV; these properties make it similar to the composition of the endoneurial tubes, which are also basement membrane layers. These gels are used in in vivo and in vitro assays to support cell migration.

The first positive control used was a Polytetrafluoroethylene (PTFE or "Teflon") tube filled with an EHS-derived gel. A DRG was cultured on top of the gel/PTFE construct. In preliminary experimentation, the first positive control construct did not hold together well during histological processing.

The second positive control used a mixture of EHS-derived gel and Collagen I gel inside a hollow tube ECM-derived medical device (in the experiment, an AxoGuard® Nerve Connector was employed). The gel adhered well to the ECM tube and provided a permeable barrier for nutrient diffusion during culture. The Collagen I in the mixture improved the mechanical properties and provided improved handling and post-histology processing characteristics. The ECM tube/EHS-Collagen I gel construct of the second positive control showed better results than the PTFE/EHS gel construct.

Negative controls were employed to demonstrate the level of non-specific staining (e.g., staining not due to the presence of migration/outgrowth of neurites from the DRG). The negative control used in each experiment included a nerve graft segment without an emplaced DRG, cultured under standard culture conditions (e.g., standard medium).

Passivation

Passivation is intended to produce a nerve graft with reduced bioactivity to further demonstrate that the bioassay is measuring the bioactivity of the graft. Generally, passivation should result in a decrease in neurite/Schwann cell extension into the nerve graft. Analysis of the experimental results should indicate a measurable difference between the passivated and non-passivated samples to help confirm the validity of the bioassay.

As the Avance® Nerve Graft used in the experiments is an insoluble solid scaffold, traditional dose response experiments cannot be conducted. As an alternative, chemical passivation 281 was used to reduce the bioactivity of the nerve graft. The treatment with formaldehyde is known to non-specifically modify and inactivate proteins, which can result in denaturation and impact bioactivity. A short treatment with 10% neutral buffered formalin (3-4% formaldehyde), was tested as a method of inactivating segments of Avance® Nerve Graft. Aldehydes, such as formaldehyde in 10% neutral buffered formalin, can chemically alter many biologics and generally reduce the bioactivity.

Unpassivated nerve grafts were treated in the standard medium 280.

Experimental Results

Staining was performed using βIII-Tubulin to show the neurite outgrowth and S100 to show the presence and location of Schwann cells in the samples. Overall, the staining quality of the βIII-Tubulin slides was acceptable for analysis.

Most negative controls showed the expected staining, (i.e., lack of staining for the presence of neurite extension or Schwann cells in the segments), except for a sample on which a DRG was inadvertently placed.

The additional positive control using an alternative tube material, an ECM tube, was investigated to replace the PTFE tube; the ECM tube was filled with EHS gel. The ECM tube filled with the gel maintained structure better than the PTFE tube, which was desirable for the positive control group. This positive control construct was effective, and the viability of the DRGs was clearly visible through migration/outgrowth into the gel.

The results of the chemical passivation demonstrate that changes anticipated to reduce the bioactivity of the Avance® Nerve Graft also reduce the outgrowth seen in the bioassay. While less specific than a possible antibody-based inhibition, this method is simple, uses inexpensive reagents, and is likely to be robust and highly reproducible.

Individual sample neurite outgrowth and Schwann cell outgrowth is shown in Table 1. Summary data is located in Table 2. The distances for a sample were obtained by averaging the three longest extension values observed in the sample. This "longest-three" average for each sample was averaged by group to obtain a group average and standard deviation. Samples were grouped by nerve graft treatment type into the standard medium group and the chemically passivated group.

As shown in Table 2, the standard culture conditions at 7 days showed neurite extension of approximately 2204 μm from the segment edge, which is approximately 73% of the total length of the segment. The range of neurite extension was 1672.3 μm to 2870.7 μm. The standard culture conditions also showed Schwann cells present at approximately 2294 μm from the segment edge, on average, which is approximately 76% of the total length of the segment. The range of Schwann cell ingrowth into the graft from the graft edge was approximately 1253 μm to 2838 μm.

TABLE 1

Individual sample data

| | Sample ID | Neurite length (βIII Tubulin)*, μm | Schwann Cell Outgrowth (S100)*, μm | Neurite Density Qualitative Score | Schwann Cell Density Qualitative |
|---|---|---|---|---|---|
| Standard Group | 281-01-01-01 | 2185.3 | 2784.3 | 3 | 3 |
| | 281-01-01-04 | 1672.3 | 2787.0 | 2 | 2 |
| | 281-01-01-08 | 2404.7 | 2838.0 | 2 | 3 |
| | 281-01-01-11 | 2005.0 | 2262.0 | 2 | 2 |
| | 281-01-01-15 | 2070.0 | 2266.0 | 2 | 3 |
| | 281-01-01-18 | 1706.0 | 1253.7 | 2 | 2 |
| | 281-01-01-22 | 2163.7 | 2581.0 | 2 | 3 |
| | 281-01-01-25 | 2133.7 | 1927.7 | 2 | 2 |
| | 281-01-01-29 | 2870.7 | 2786.3 | 3 | 3 |
| | 281-01-01-32 | 2835.7 | 2410.3 | 2 | 3 |
| | 281-01-01-36 | 2038.0 | 1838.0 | 2 | 2 |
| | 281-01-01-39 | 2366.0 | 1801.7 | 2 | 2 |
| Chemical Passivated Group | 281-01-01-03 | 1315.7 | 1087.4 | 1 | 1 |
| | 281-01-01-06 | 1486.3 | 980.9 | 1 | 1 |
| | 281-01-01-10 | 1148.7 | 317.4 | 1 | 2 |
| | 281-01-01-13 | 1292.3 | 646.0 | 1 | 1 |
| | 281-01-01-17 | 878.4 | 853.1 | 1 | 2 |
| | 281-01-01-20 | 1191.7 | 570.1 | 1 | 1 |
| | 281-01-01-24 | 1123.7 | 904.7 | 1 | 1 |
| | 281-01-01-27 | 1078.3 | 1422.5 | 1 | 1 |
| | 281-01-01-31 | 1376.7 | 522.5 | 1 | 1 |
| | 281-01-01-34 | 1320.3 | 1221.0 | 1 | 2 |
| | 281-01-01-38 | 1423.0 | 914.2 | 1 | 1 |
| | 281-01-01-41 | 1128.9 | 945.6 | 1 | 1 |

TABLE 2

Summary Data

| Culture Condition | Neurite length (μm) +/− SD | Neurite Density Qualitative Score | Schwann Cell outgrowth (μm) +/− SD | Schwann Cell Density Qualitative Score | % of graft segments with evidence of DRG |
|---|---|---|---|---|---|
| Standard, 7 day | 2204.3 ± 373.3 | 2.2 | 2294.7 ± 503.3 | 2.5 | 100 |
| Chemically Passivated | 1230.3 ± 170.6 | 1.0 | 865.5 ± 310.9 | 1.3 | 100 |

Passivation Analysis—The total data set was analyzed using a one factor ANOVA, which indicates that there is a significant difference within the data (p<0.001 for both neurite and Schwann cell data, see Table 2). T-test with Bonferroni correction assuming equal variances indicates that the "chemically passivated" group is significantly different from the "standard medium" group (neurite lengths, uncorrected P<0.00001; Schwann cell outgrowth, uncorrected P<0.00001).

Furthermore, during the examination of the slide images, some of the samples had the longest neurites inside of the fascicles while others had the longest neurites outside or along the surface of the fascicles. The longest neurites were marked regardless of the neurite location (i.e. inside or outside the endoneurium), but the location of the neurite (inside or outside the endoneurium) was also recorded. Each group was analyzed for the percent of neurites outside of the fascicle as compared to inside the fascicle. The standard medium group had 13.9% of the longest neurites outside of the fascicle. The antibody passivated group had 3.3% of the longest neurites outside of the fascicle. The chemically passivated group had the highest percentage of the longest neurites outside of the fascicle, at 80.6% of the longest neurites. This result supports the analysis that chemical passivation has effectively reduced the bioactivity of the inner surface of the endoneurium by affecting the laminin, deterring growth down the desired growth path.

To summarize, the methods used for assembly and culture of the constructs are reproducible and result in observable outgrowth of neurites and Schwann cells into a nerve graft sample. The 7-day culture in Standard medium provides a high signal with the measurement of the longest neurite and Schwann cell migration into the nerve graft sample. The histology preparation and staining methods resulted in acceptable staining for use in the analysis by the defined scoring methodology. Both the βIII-Tubulin and S100 staining resulted in similar measurements and conclusions. The formaldehyde-based passivation of the nerve grafts results in a reproducible and significant attenuation of the bioactivity of the graft. The use of ECM/Collagen gels in AxoGuard® segments generated acceptable positive controls, which demonstrated the viability of the cultured DRGs even though larger gel volume may be desirable.

It should be understood that the examples and embodiments described herein are for illustrative purposes only and that various modifications or changes in light thereof will be suggested to persons skilled in the art and are to be included within the spirit and purview of this application.

Although the subject matter has been described in language specific to structural features and/or acts, it is to be understood that the subject matter defined in the appended claims is not necessarily limited to the specific features or acts described above. Rather, the specific features and acts described above are disclosed as examples of implementing the claims and other equivalent features and acts are intended to be within the scope of the claims.

What is claimed is:

1. A method for conducting an in vitro bioassay, the method comprising:
   affixing a dorsal root ganglion (DRG) to a first end of an acellular nerve graft segment with a collagen gel to form a test construct;
   culturing the test construct in a neuron cell growth medium for a period of time to allow nerve outgrowth from the DRG into the nerve graft segment;
   performing an analysis of the test construct, wherein the analysis indicates an amount of a peripheral nerve structure outgrowing from the DRG, wherein performing the analysis of the test construct comprises:
      identifying at least three longest nerve structures outgrowing from the DRG into the nerve graft segment,
      measuring a length from the first end of the nerve graft segment on which the DRG is affixed to an end of each of the at least three longest nerve structures outgrowing from the DRG within the nerve graft segment, and
      averaging the measured length of the at least three longest nerve structures; and
   determining a potency of the nerve graft from a metric derived from the analysis.

2. The method of claim 1, wherein performing the analysis of the test construct further comprises:
   preparing the test construct for sectioning;
   sectioning the test construct into a plurality of sections, wherein each of the plurality of sections is removed longitudinally at a predetermined distance from a side of the nerve graft segment perpendicular to the first end; and
   staining each section with one or more stains to identify the peripheral nerve structure outgrowing from the DRG.

3. The method of claim 2, wherein preparing the test construct for sectioning comprises fixing the test construct and paraffin-embedding the test construct.

4. The method of claim 2, wherein each of the plurality of sections is from about 4 μm to about 8 μm thick.

5. The method of claim 1, wherein performing the analysis of the test construct comprises:
   scanning all or part of the test construct with diffusion tensor imaging and producing a tractography image wherein the outgrowing peripheral nerve structure is identified by the tractography image; and
   quantifying the amount of outgrowing peripheral nerve structure from the tractography image.

6. The method of claim 1, wherein the DRG is obtained from a fluorescent transgenic animal expressing a fluorophore in neuronal cells, wherein performing the analysis of the test construct comprises:
   scanning all or part of the test construct with fluorescence microscopy and producing one or more images wherein the outgrowing peripheral nerve structure is identified by the fluorophore; and
   quantifying the amount of outgrowing peripheral nerve structure from the one or more images.

7. The method of claim 6, wherein the fluorescence microscopy is selected from the group consisting of confocal fluorescence microscopy, two-photon fluorescence microscopy, and super-resolution fluorescence microscopy with deconvolution.

8. The method of claim 1, wherein performing the analysis of the test construct comprises:
   extracting, from the test construct, mRNA for a target protein associated with the outgrowing peripheral nerve structure; and
   determining a quantity of the mRNA for the target protein using an rtPCR assay.

9. The method of claim 8, wherein the target protein is selected from the group consisting of βIII-Tubulin, S100, and GAP-43.

10. The method of claim 1, wherein performing the analysis of the test construct comprises:
    extracting, from the test construct, a target protein associated with the outgrowing peripheral nerve structure; and determining a quantity of the target protein using an ELISA assay.

11. The method of claim 10, wherein the target protein is selected from the group consisting of βIII-Tubulin, S100, and GAP-43.

12. The method of claim 1, wherein the outgrowing peripheral nerve structure is a neurite or a Schwann cell.

13. The method of claim 1, further comprising passivating the nerve graft segment with a chemical solution prior to affixing the DRG onto the nerve graft segment.

14. The method of claim 13, wherein the chemical solution comprises about 10% neutral buffered formalin.

15. The method of claim 1, further comprising passivating the nerve graft segment with a functional blocking anti-laminin antibody or a functional blocking anti-integrin antibody.

16. The method of claim 1, wherein the period of time for culturing is from about 3 to about 7 days.

17. The method of claim 1, wherein the nerve graft segment is taken from an acellular nerve allograft that has been processed to remove:
   cellular debris that may impede outgrowth of the peripheral nerve structure, and
   material and/or molecules that may elicit a deleterious immune response in a recipient of the nerve graft.

18. The method of claim 5, wherein the medium comprises at least Nerve Growth Factor (NGF), and wherein the NGF is provided at a concentration of about 25 ng/mL.

19. The method of claim 1, wherein the medium comprises B-27, glutamine, and Nerve Growth Factor (NGF).

* * * * *